United States Patent [19]

Dietliker et al.

[11] Patent Number: 4,736,055
[45] Date of Patent: Apr. 5, 1988

[54] OXIME SULFONATES CONTAINING REACTIVE GROUPS

[75] Inventors: Kurt Dietliker; Werner Rutsch, both of Fribourg; Godwin Berner, Binningen; Max Hunziker, Bösingen, all of Switzerland; Christopher G. Demmer, Cambridge, England

[73] Assignee: Ciba-Geigy Corporation, Ardsley, N.Y.

[21] Appl. No.: 851,032

[22] Filed: Apr. 11, 1986

[30] Foreign Application Priority Data

Apr. 12, 1985 [CH] Switzerland ............... 1580/85

[51] Int. Cl.[4] .......................... C07C 131/00
[52] U.S. Cl. .......................... 560/13; 544/146; 544/152; 544/159; 546/206; 546/212; 546/213; 546/214; 546/226; 548/517; 548/527; 548/546; 549/60; 549/72; 549/75; 549/76; 549/488; 549/491; 549/496; 549/551; 549/552; 558/7; 558/48; 558/49; 558/51; 558/52; 558/55; 558/56; 558/57; 558/58; 560/10; 560/12; 560/118; 560/125; 560/139; 560/145; 560/149; 560/151; 560/220; 560/221; 560/222; 560/355; 560/358; 560/330; 562/427; 562/428; 562/430; 562/500; 562/507; 562/556; 564/154; 564/162; 564/191; 564/192; 564/194; 564/197; 564/198; 564/204; 564/207; 564/208; 564/254; 260/543 R; 260/544 L; 260/544 D; 260/544 B; 260/544 S; 260/544 Y; 260/545 R; 526/256; 526/260; 526/263; 526/270; 526/280; 526/287; 204/159.16; 427/54.1

[58] Field of Search .............. 560/10, 12, 13, 149, 560/140, 221, 222, 118, 125, 139, 145, 151, 220, 355, 330, 358; 562/427, 428, 430, 507, 500, 556; 260/544 L, 544 B, 544 P, 544 S, 544 Y, 543 R, 545 R; 564/224, 220, 154, 191, 254, 206, 192, 204, 208, 194, 197, 198, 207; 549/488, 491, 551, 72, 75, 76, 60, 59, 496, 552; 544/146, 152, 159; 546/206, 212, 213, 214, 226; 548/517, 527, 546; 558/7, 48, 49, 51, 52, 55, 56, 57, 58

[56] References Cited

U.S. PATENT DOCUMENTS

| | | | |
|---|---|---|---|
| 3,497,554 | 2/1970 | Remers | 564/254 |
| 3,983,246 | 9/1976 | Gibbons | 514/601 |
| 4,017,652 | 4/1977 | Gruber | 427/54 |
| 4,026,705 | 5/1977 | Crivello et al. | 96/27 |
| 4,289,865 | 9/1981 | Wilson et al. | 526/288 |
| 4,351,935 | 9/1982 | Reesink et al. | 528/242 |
| 4,353,787 | 10/1982 | Alexander et al. | 204/159.15 |
| 4,504,372 | 3/1985 | Kirchmayr et al. | 204/159.15 |
| 4,540,598 | 9/1985 | Berner et al. | 427/54.1 |

FOREIGN PATENT DOCUMENTS

| | | |
|---|---|---|
| 1392479 | 4/1975 | United Kingdom . |
| 1472951 | 5/1977 | United Kingdom . |
| 1472952 | 5/1977 | United Kingdom . |

OTHER PUBLICATIONS

Organic Synthesis, 59, 95 (1979).

Primary Examiner—Michael L. Shippen
Attorney, Agent, or Firm—Luther A. R. Hall

[57] ABSTRACT

Oxime sulfonates of formula I

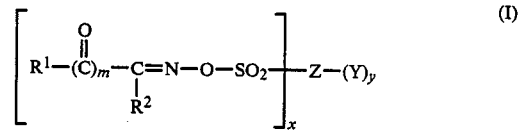

wherein Y is a polymerizable unsaturated group or epoxide group or an —OH, —NHR[5], —COOH, COOR[6], —COCl, —CH₂Hal, —SO₂Cl or —NCO group, Z is an (x+y)-valent connecting member, R[1] and R[2] are monovalent organic radicals, m is 0 or 1, x is 1 or 2 and y is 1 or 2, can be converted into polymers which can be thermally or photochemically dissociated to form free sulfonic acid groups. Said polymers can therefore be used as photoresists which can be developed with aqueous alkalis.

10 Claims, No Drawings

OXIME SULFONATES CONTAINING REACTIVE GROUPS

The invention relates to novel sulfonic acid esters of oximes. The novel esters contain in the sulfonic acid radical a polymerisable group or a group which can react with functional groups of a polymer or with the precursors thereof. The invention also relates to the polymers which can be prepared from these novel esters and to the use of said polymers for the photochemical production of images.

European patent applicatons EP-A1 No. 44 115 and EP-A1 No. 139 609 disclose oxime sulfonates which are thermally or photolytically dissociated to form the free sulfonic acids and which can be used as curing catalysts for acid-curable varnishes. For this purpose it is preferred to use esters of non-reactive sulfonic acids in order to avoid reactions with surface-coating resins, which reactions can disturb the curing of the varnishes.

However, if the oximes are esterified with sulfonic acids containing a functional group which is either a polymerisable or polycondensable group or which can react with specific polymers with bonding, then polymers containing an oxime sulfonate side group can be prepared therefrom, which polymers can be converted by irradiation or heating into polymers containing sulfonic acid side groups. There are a number of interesting uses for such polymeric oxime sulfonates.

The present invention relates primarily to the monomers, i.e. to oxime sulfonates which carry in the sulfonic acid radical specific functional groups. Said oxime sulfonates are compounds of formula I

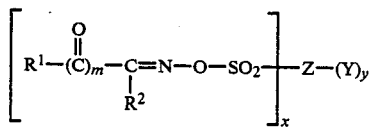

wherein m is 0 or 1, x is 1 or 2 and y is 1 or 2, $R^1$ is $C_1-C_{12}$alkyl, $C_1-C_4$haloalkyl, $C_5-C_{12}$cycloalkyl, $C_6-C_{10}$aryl which is unsubstituted or substituted by one or more of the substituents selected from the group consisting of halogen, $C_1-C_{16}$alkyl, $C_1-C_4$alkoxy, phenoxy, phenyl and nitro, or $R^1$ is furyl, thienyl, $C_7-C_{12}$aralkyl, $C_1-C_8$alkoxy, $C_5-C_8$-cycloalkoxy, phenoxy or —CN, $R^2$ has one of the meanings indicated for $R^1$, or is $C_2-C_6$alkanoyl, benzoyl, $C_2-C_5$alkoxycarbonyl, phenoxycarbonyl, $-N(R^3)(R^4)$, morpholino or piperidino, or $R^1$ and $R^2$, together with the atoms to which they are attached, form a 5- to 8-membered ring which may be fused with 1 or 2 radicals of the benzene series, $R^3$ being hydrogen, $C_1-C_{12}$alkyl, phenyl, $C_2-C_6$alkanoyl or benzoyl and $R^4$ being hydrogen, $C_1-C_{12}$alkyl or cyclohexyl, Y is a polymerisable ethylenically unsaturated group or epoxide group or an —OH, $-NHR^5$, —COOH, $-COOR^6$, —COCl, $-CH_2Hal$, $-SO_2Cl$ or —NCO group, in which formulae $R^5$ is hydrogen, $C_1-C_6$alkyl or phenyl, $R^6$ is $C_1-C_6$alkyl or phenyl and Hal is chlorine or bromine, and Z is an (x+y)-valent organic connecting member which links the sulfo radical $-SO_2-$ with the group Y.

The connecting member Z is preferably an (x+y)-valent aromatic, aliphatic, cycloaliphatic or araliphatic group which may be interrupted by O, S, CO, $SO_2$ or $NR^5$ or may be substituted by halogen, alkyl, phenyl, hydroxy, alkoxy or aryloxy. $R^1$, $R^2$, $R^3$, $R^4$, $R^5$ and $R^6$ as alkyl may be straight chain or branched alkyl and, depending on the number of carbon atoms indicated, may be e.g. methyl, ethyl, propyl, isopropyl, n-butyl, sec-butyl, tert-butyl, n-pentyl, isoamyl, n-hexyl, 2-ethylbutyl, n-octyl, 2-ethylhexyl, n-decyl or n-dodecyl.

$R^1$ or $R^2$ as $C_1-C_4$haloalkyl may be e.g. chloromethyl, trichloromethyl, trifluoromethyl or 2-bromopropyl.

$R^1$ and $R^2$ as cycloalkyl may be e.g. cyclopentyl, cyclohexyl, cyclooctyl or cyclododecyl.

$R^1$ and $R^2$ as unsubstituted or substituted aryl may be e.g. phenyl, 4-fluorophenyl, 4-chlorophenyl, 2,4-dichlorophenyl, 2,6-dichlorophenyl, p-tolyl, 2,4-dimethylphenyl, 4-isopropylphenyl, 4-tertbutylphenyl, 4-dodecylphenyl, 4-methoxyphenyl, 4-butoxyphenyl, 4-phenoxyphenyl, 4-biphenylyl, 3-nitrophenyl, 1- or 2-naphthyl, 5-chloro-1-naphthyl, 6-bromo-2-naphthyl, 4-nitro-1-naphthyl or 6-methoxy-2-naphthyl. $R^1$ as furyl or thienyl is preferably 2-furyl or 2-thienyl.

$R^1$ and $R^2$ as aralkyl may be e.g. benzyl, 1- or 2-phenylethyl, 3-phenylpropyl, 2-phenylisopropyl, 2-phenylhexyl or naphthylmethyl.

$R^1$ or $R^2$ as alkoxy is preferably methoxy or ethoxy. $R^1$ or $R^2$ as cycloalkoxy is preferably cyclohexyloxy. $R^2$ as alkoxycarbonyl is preferably methoxycarbonyl or ethoxycarbonyl. If $R^1$ and $R^2$, together with the atoms to which they are attached, form a 5- to 8-membered ring, then this may be an isocyclic or heterocyclic ring, e.g. a cyclopentane, cyclohexane, cycloheptane, pyran or piperidine ring. This ring may also be fused with radicals of the benzene series. Examples of this are tetrahydronaphthalene, dihydroanthracene, indan, chroman, fluorene, xanthene or thioxanthene ring systems. The ring may also contain carbonyl groups. Examples of this are benzoquinone, naphthoquinone or anthraquinone radicals. $R^2$ and $R^3$ as alkanoyl may be e.g. acetyl, propionyl, butyryl or hexanoyl.

Y as a polymerisable group may be an ethylenically unsaturated group or an epoxide group. The group Y may be present in the molecule once or twice. If Y is an ethylenically unsaturated group, y is mainly 1. Examples of ethylenically unsaturated polymerisable groups are vinyl, allyl, vinyloxy, vinyloxycarbonyl, allyloxy, allylamino, diallylamino, acryloxy, methacryloxy, acrylamido, methacrylamido, maleinimido or itaconimido. Examples of polymerisable epoxide groups are the groups

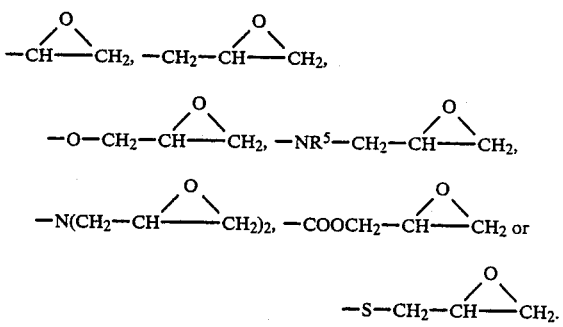

y is preferably 1 and Y is preferably a group of the formula

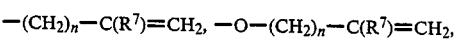

-continued
—O—CO—C(R⁷)=CH₂, —NH—CO—C(R⁷)=CH₂,
—N(CH₂CH=CH₂)₂, —CO—O—(CH₂)ₙ—C(R⁷)=CH₂,

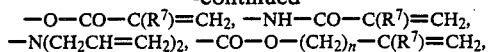

in which formulae R⁷ is hydrogen or CH₃ and n is 0 or 1.

Compounds of formula I, wherein Y is such an ethylenically unsaturated group, can be subjected to radical homopolymerisation or copolymerisation.

If Y is an epoxide group or an —OH, —NHR⁵, —COOH, —COOR⁶, —COCl, —CH₂Hal, —SO₂Cl or —NCO group, then this radical may be present in the molecule once or twice, depending on the meaning of y. If y is 2, then these compounds are suitable for a polycondensation or polyaddition reaction with another difunctional compound. If e.g. y is 2 and Y is —OH, then the compounds of formula I are diols which can be reacted with dicarboxylic acids or with derivatives thereof to give polyesters or with diepoxides to give polyethers or with diisocyanates to give polyurethanes. If the compounds of formula I are diamines, they can be reacted with dicarboxylic acids or with derivatives thereof to give polyamides, with diepoxides to give polyamines or with diisocyanates to give polyureas. If the compounds of formula I are dicarboxylic acids, they can be reacted with diamines to give polyamides and with diepoxides to give polyesters. If the compounds of formula I are dicarboxylic acid esters (Y=—COOR⁶) or dicarboxylic acid chlorides (Y=—COCl), they can be reacted with diols to give polyesters and with diamines to give polyamides. If the compounds are dihalides, they can be reacted with diols to give polyethers and with diamines to give polyamines. If the compounds are diisocyanates (Y=—NCO), they can be reacted with diols to give polyurethanes and with diamines to give polyureas. This constitutes only a selection of possibilities for forming linear polymers from difunctional compounds of formula I. The skilled person will be in a position to choose a suitable polymerisation reaction and suitable reaction partners for the required purpose.

If y is 1 and Y is an epoxide group or an —OH, —NHR⁵, —COOH, —COOR⁶, —COCl, —CH₂Hal, —SO₂Cl or —NCO group, the compounds of formula I are suitable for reaction with specific polymers, with bonding of the molecule of formula I to the polymer.

If e.g. the polymer contains free hydroxyl groups, as is the case with for example cellulose and cellulose derivatives, partial esters of polyvinyl alcohol, or copolymers of 2-hydroxyethyl acrylate, or novolak resins or epoxy resins, then e.g. compounds of formula I, wherein Y is —COCl, —CH₂Hal, —NCO, —SO₂Cl or —COOR⁶, can be reacted with such polymers.

If the polymer contains anhydride groups, e.g. copolymers of maleic anhydride, then bonding can be achieved with compounds of formula I, wherein Y is —OH or —NHR⁵. If the polymer contains free carboxyl groups, e.g. copolymers of acrylic acid, then e.g. compounds of formula I, wherein Y is an epoxide group, can be reacted with it. If the polymer contains epoxide groups, e.g. copolymers of glycidyl methacrylate, then it can be reacted e.g. with compounds of formula I, wherein Y is —NHR⁵ or —COOH.

Examples of connecting members Z are 2-, 3- or 4-valent aromatic or aromatic-aliphatic groups, e.g. the groups of the formulae

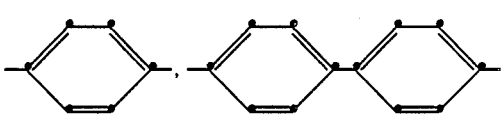

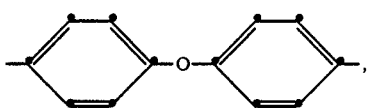

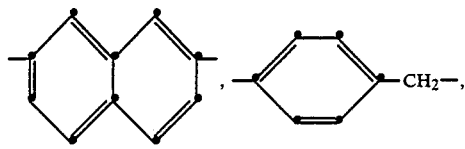

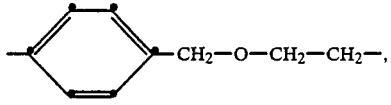

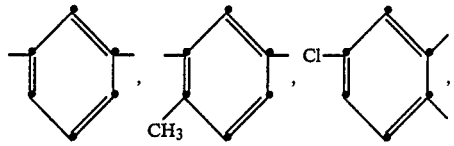

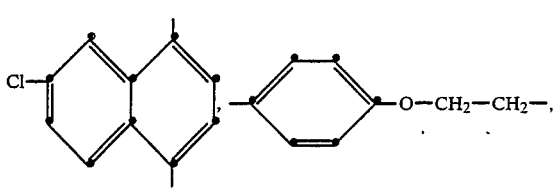

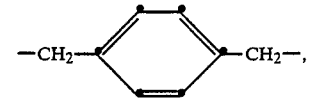

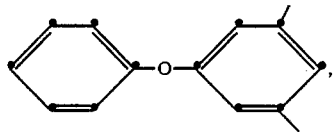

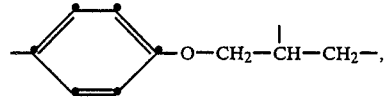

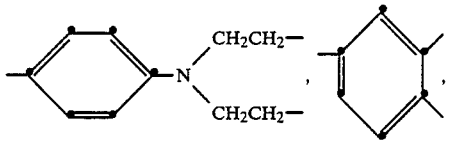

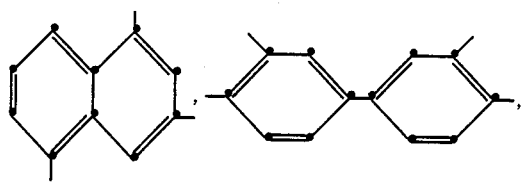

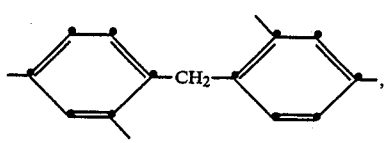

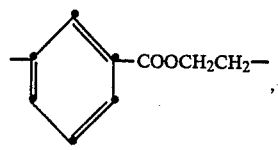

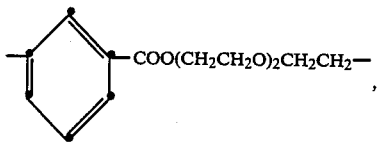

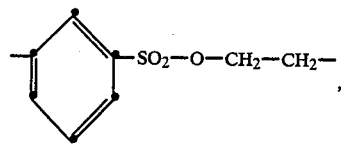

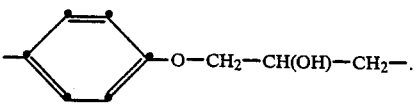

Examples of aliphatic or cycloaliphatic radicals Z are the groups —CH$_2$—, —(CH$_2$)$_2$—, —(CH$_2$)$_3$—, —(CH$_2$)$_4$—, —(CH$_2$)$_6$—, —(CH$_2$)$_8$—, —CH$_2$CH$_2$—O—CH$_2$CH$_2$—, —(CH$_2$CH$_2$O)$_2$CH$_2$CH$_2$—, —CH$_2$CH$_2$SCH$_2$CH$_2$—, —CH$_2$CH$_2$NHCH$_2$CH$_2$—, —CH$_2$—CH(CH$_3$)—CH$_2$—,

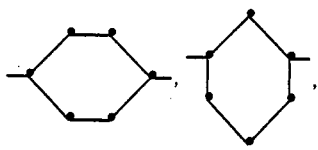

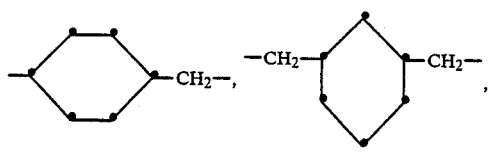

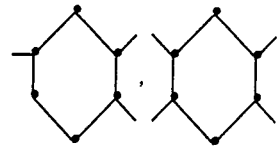

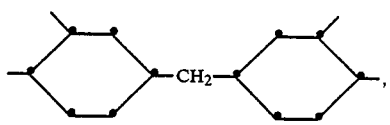

—CH$_2$CH$_2$OCH$_2$CHCH$_2$—, C$_2$H$_5$—C(CH$_2$—)(CH$_2$—)—CH$_2$,

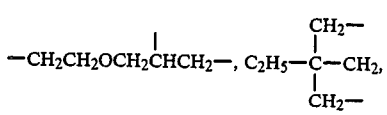

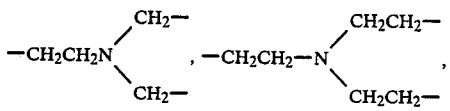

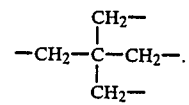

If x and y are 1, then Z is a divalent radical and has the following preferred meanings: C$_6$-C$_{12}$arylene which is substituted by C$_1$-C$_{16}$alkyl or halogen, or C$_7$-C$_{12}$arylenealkylene, C$_8$-C$_{12}$arylenedialkylene or oxydiphenylene, or straight chain or branched C$_1$-C$_{12}$alkylene which may be interrupted by O, S, CO, SO$_2$ or NR$^5$ or may be substituted by phenyl, halogen, phenoxy, C$_1$-C$_4$alkoxy or OH.

Preferred compounds of formula I are those wherein R$^1$ is C$_1$-C$_6$alkyl, C$_1$-C$_4$haloalkyl, phenyl which is unsubstituted or substituted by 1 or 2 substituents selected from the group consisting of chlorine, C$_1$-C$_4$alkyl, C$_1$-C$_4$alkoxy and NO$_2$, or is 2-furyl, 2-thienyl, C$_1$-C$_4$alkoxy or —CN, R$^2$ has one of the meanings indicated for R$^1$ or is dialkylamino or morpholino, or R$^1$ and R$^2$, together with the atoms to which they are attached, form a 5- or 6-membered ring which may be fused with 1 or 2 radicals of the benzene series.

Particularly preferred compounds of formula I are those wherein m is 0 or 1, R$^1$ is C$_1$-C$_4$alkyl, trifluoromethyl, phenyl, monochlorophenyl, dichlorophenyl or methoxyphenyl, R$^2$ has one of the meanings indicated for R$^1$ or is —CN, or R$^1$ and R$^2$, together with the carbon atom to which they are attached, form an indene, fluorene, tetraline or dihydroanthracene ring.

Examples of individual compounds of formula I are the following compounds:

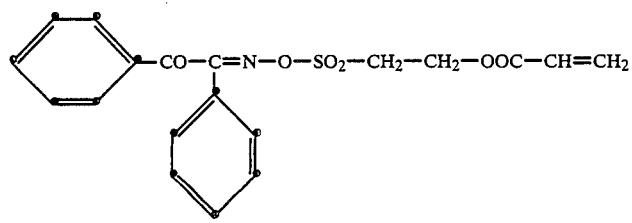
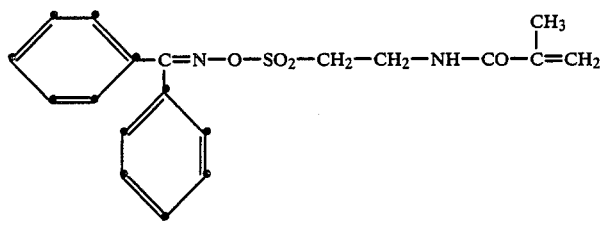
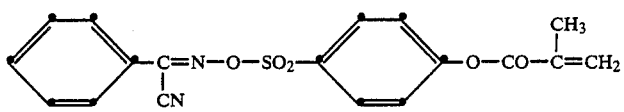
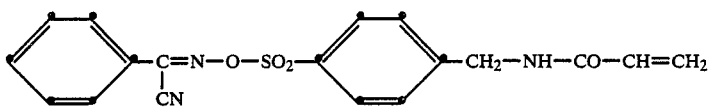
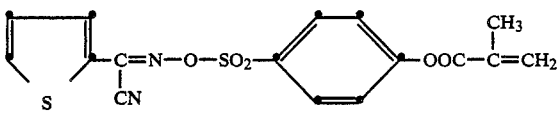
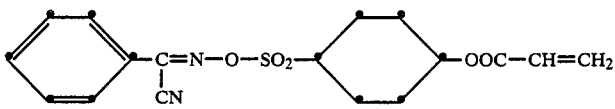
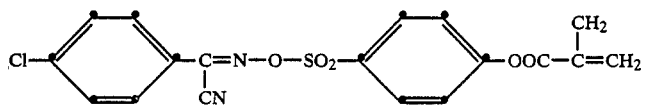
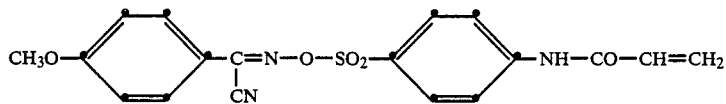
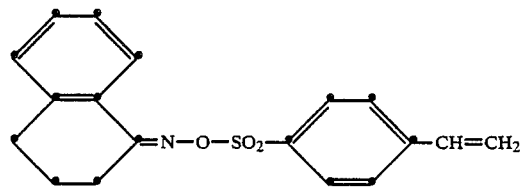
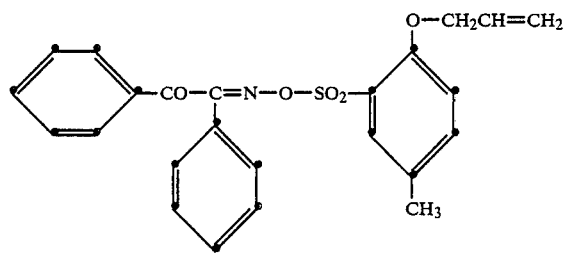
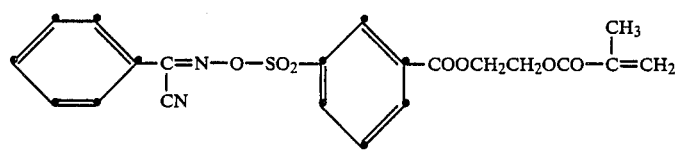

-continued
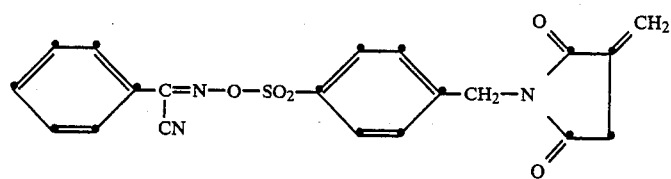
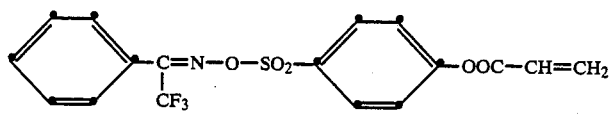
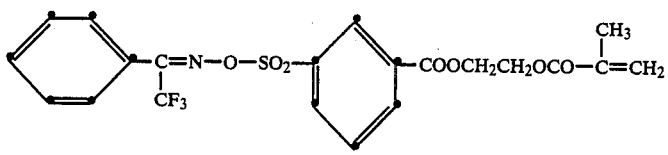
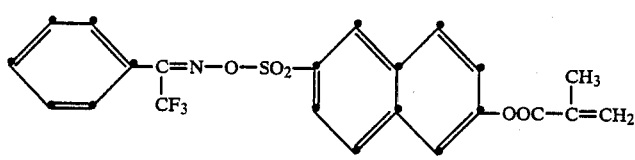
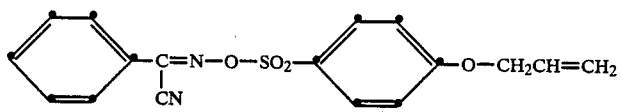
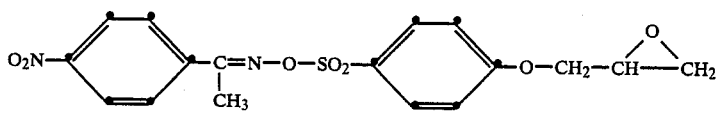
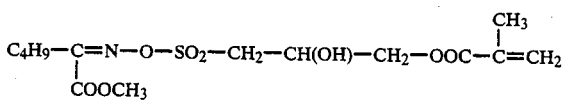
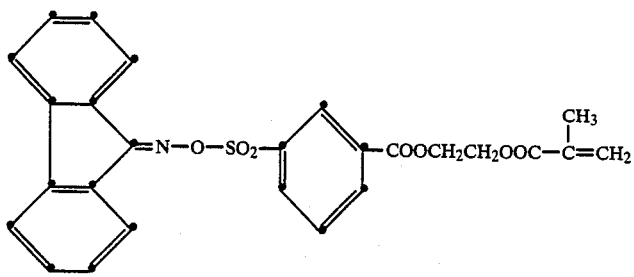
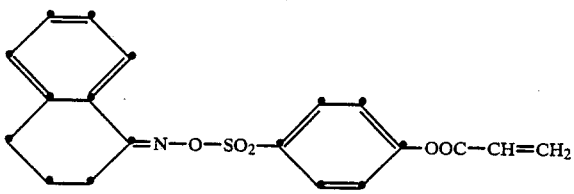

-continued
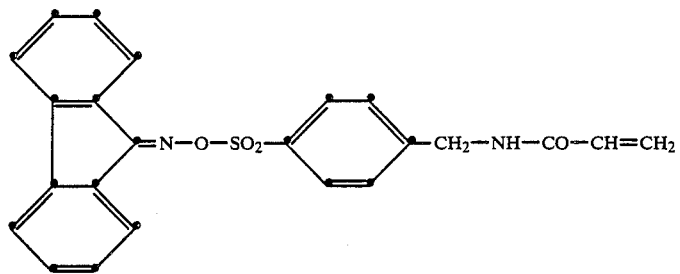
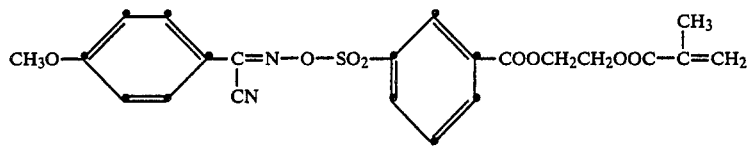
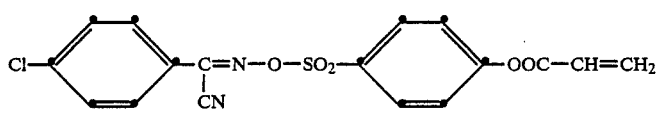
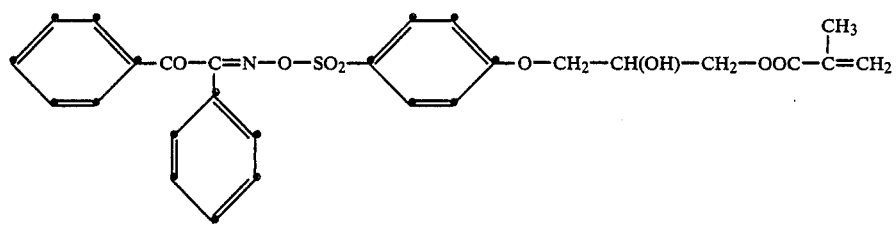
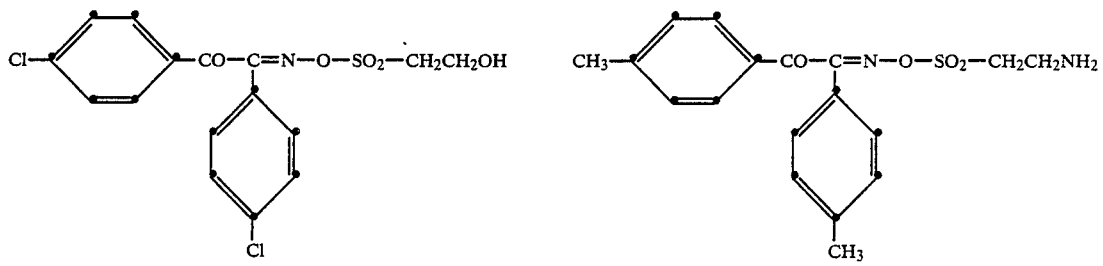
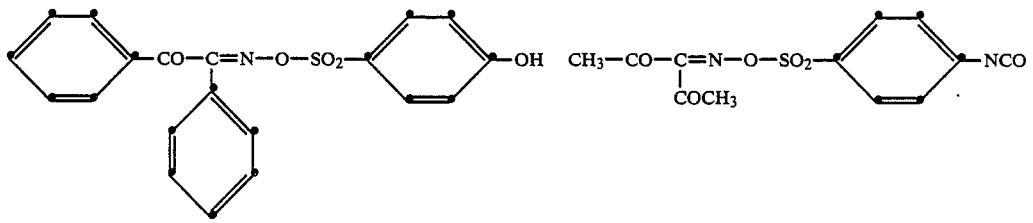
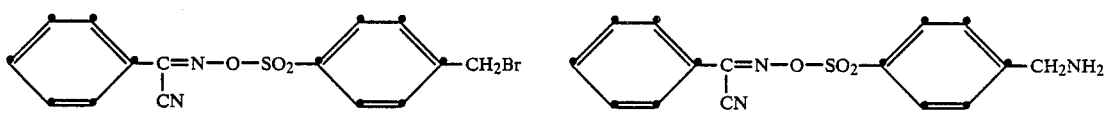
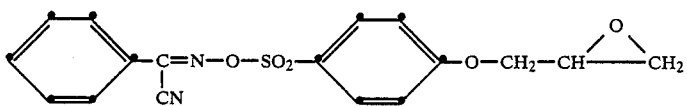

-continued
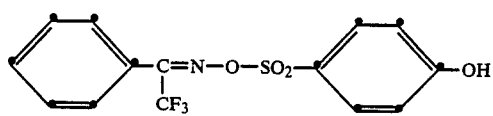
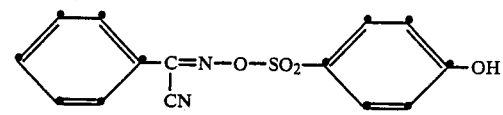
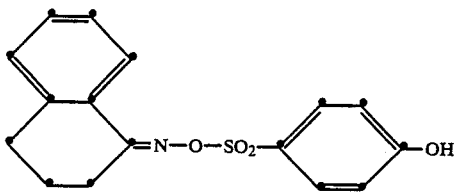
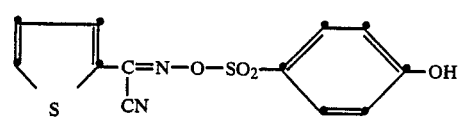
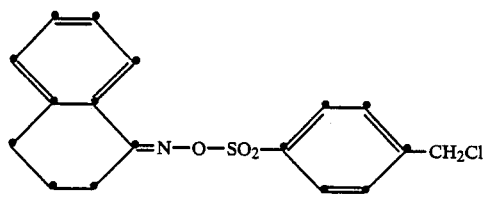
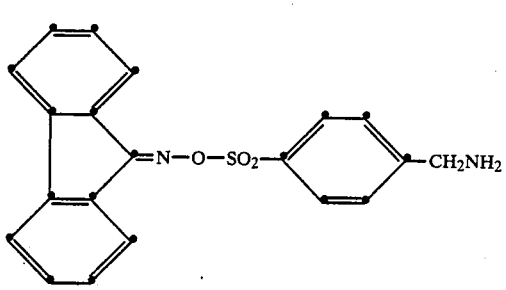
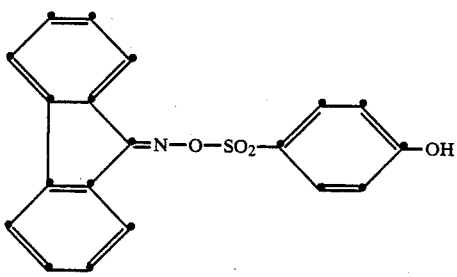
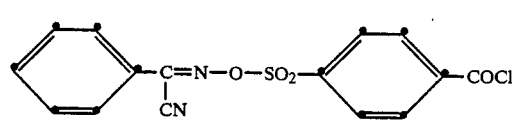
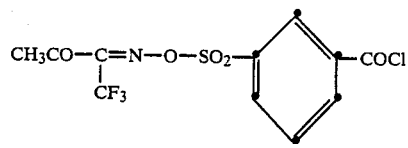
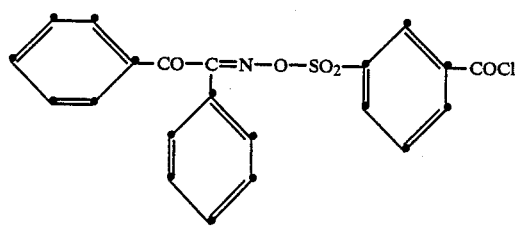
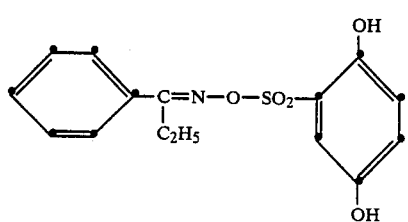
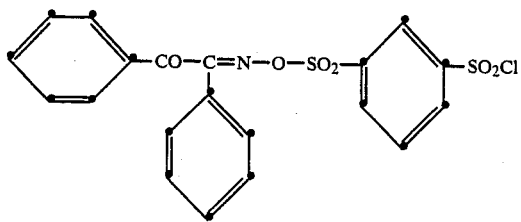

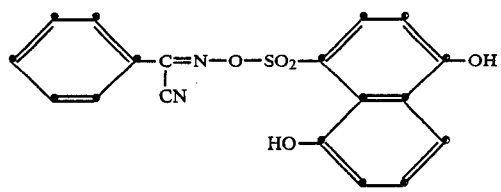
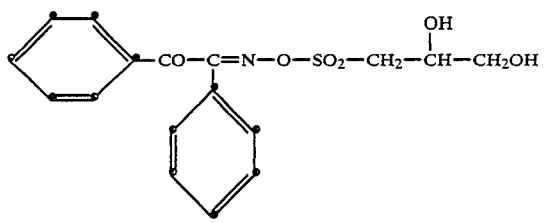
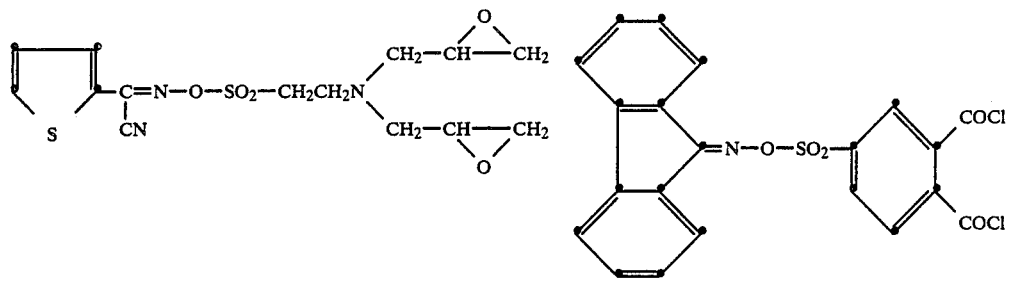
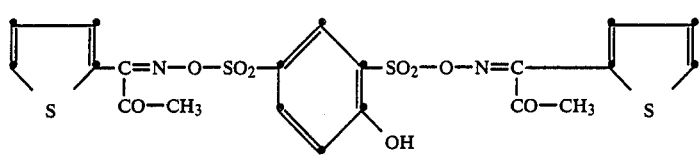
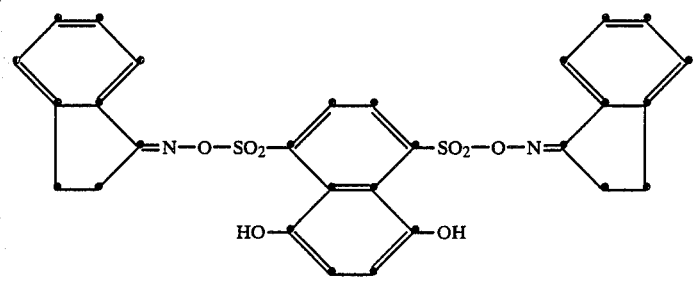
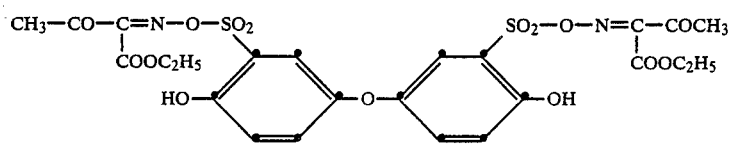
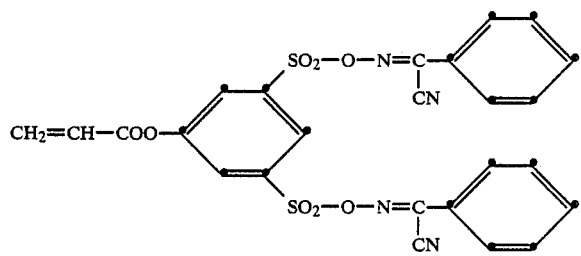
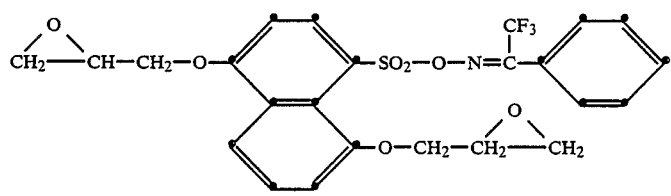
There are various ways of preparing the compounds of formula I. For example, an oxime compound of for-

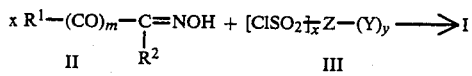

II  III

This reaction can also be carried out with a sulfonyl chloride of the formula

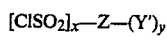

in which case the group Y' is subsequently converted into a group Y. Y' may for example be an —OH group which is subsequently esterified with acrylic or methacrylic acid or which is subsequently converted by reaction with epichlorohydrin and alkali metal hydroxide into the glycidyl ether. If Y' is an NH$_2$ group, this can be acylated e.g. with acryloyl chloride or methacryloyl chloride or one or two glycidyl groups can be introduced by reaction with epichlorohydrin. If Y' is a carboxyl group, this can be converted into a —COCl or —COOR$^6$ group. Isocyanate groups can be prepared by phosgenating a group Y'=NH$_2$. If the group Y' is halogen, this can be converted into an OH or NHR$^5$ group. The methods of introducing Y listed here constitute merely several examples of many possible methods which are chosen according to whether Z is an aromatic or aliphatic radical and according to which type of reactive group Y is desired. In general, the introduction of Y into the sulfonic acid radical can be effected either before or after the sulfonylation of the oxime. There also exist a number of sulfonic acids substituted by Y which are commercially available industrial products, e.g. taurine, isethionic acid, sulfalinic acid, metalinic acid, and various phenolsulfonic acids, naphtholsulfonic acids and naphthylaminesulfonic acids.

As mentioned above, the compounds of formula I can be converted into polymers containing side chains in which oxime sulfonate groups are present. When subjected to heating or irradiation, in particular UV irradiation, the oxime sulfonate groups are dissociated to form the free sulfonic acids. Polymers containing sulfonic acid groups are thereby formed. Said polymers are soluble in aqueous alkalis, e.g. in Na$_2$CO$_3$ solution or dilute NaOH solution. The oxime sulfonate polymers can therefore be used as photoresists which, after UV irradiation, can be developed with aqueous alkalis to produce positive images. Such photoresists are necessary for the production of printed circuits or other electronic components, and also for the production of printing plates and for use in other photographic recording processes.

Accordingly, the invention also relates to polymers containing in side groups radicals of formula IV

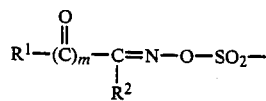

wherein m, R$^1$ and R$^2$ are as defined above.

Preferred polymers are those which are formed by polymerisation of a compound of formula I, wherein Y is an ethylenically unsaturated group, or by copolymerisation of such a compound with another ethylenically unsaturated compound.

Among such polymers, those are preferred which are formed by copolymerisation of a compound of formula I, wherein Y is an ethylenically unsaturated group, with one or more α,β-unsaturated carboxylic acids or with derivatives thereof, in particular by copolymerisation with acrylic acid, methacrylic acid or with alkyl esters thereof.

Further polymers which are preferred are those which are formed by reacting a hydroxyl group-containing polymer with a compound of formula I, wherein Y is a —COCl, —SO$_2$Cl or —NCO group.

The polymers of the present invention may have high molecular weights in the range from 10,000 to 1,000,000. They may also be relatively low molecular prepolymers which, after irradiation and development, can be converted into a high molecular state, for example by a crosslinking reaction at elevated temperature.

Light sources suitable for effecting irradiation are those with a high proportion of shortwave light. There are appropriate technical devices and various types of lamp available today for this purpose, e.g. carbon arc lamps, xenon arc lamps, mercury vapour lamps, metal halide lamps, fluorescent lamps, argon filament lamps or photographic floodlight lamps. Laser light sources have also been in use lately. These have the advantage that no photomasks are necessary; the guided laser beam writes directly onto the polymer layer.

In certain cases it is advantageous to add a photosensitiser to the polymer. By doing so, the irradiation times can be shortened or other light sources can be used. Examples of known photosensitisers are aromatic ketones and aldehydes (such as those described e.g. in U.S. Pat. No. 4,017,652), acylcoumarines, thioxanthones, fused aromatic compounds, e.g. perylene, anthracene, aromatic amines or cationic dyes such as those described e.g. in U.S. Pat. No. 4,026,705. Such sensitisers increase the sensitivity of the polymer for the photochemical production of the latent image without reducing the storage stability of said polymer. By specifically selecting a photosensitiser, the spectral sensitivity of the polymer can be shifted to desired wavelength ranges.

In addition to sensitisors, further additives customarily employed for light-sensitive substances may be added to the oxime sulfonate polymers. Examples of such additives are dyes, pigments, antihalation adjuvants, polymeric binders, reactive diluents, adhesion promoters or flexibilisers.

The oxime sulfonate polymers can also be used for the production of negative images if the polymeric sulfonic acids which form when said oxime sulfonate polymers are subjected to exposure are employed as curing catalysts for acid-curable resins, e.g. for phenoplasts, aminoplasts or epoxy resins.

Apart from their use in various photographic recording processes, the oxime sulfonate polymers may be used in combination with a pH-sensitive dye as indicators for the control of articles sensitive to heating or irradiation or for thermographic systems. Both the monomeric oxime sulfonates of formula I and the polymers prepared therefrom can be employed as latent acid catalysts for the curing of acid-curable stoving varnishes. Examples of such stoving varnishes are in particular varnishes based on melamine resins and mixtures thereof with acrylic resins, alkyd resins and polyester resins. About 0.1 to 10%, based on the surface-coating resin, of an oxime sulfonate is added to such varnishes. After the application of the varnish, the varnish film is briefly irradiated with shortwave light, in particular with UV light, and subsequently cured by heating.

Heating is preferably effected in the temperature range from 80° to 120° C.

The following Examples describe in detail the preparation of the monomers, the conversion thereof into polymers and the use of said polymers. Parts are by weight.

EXAMPLE 1
α-(3-[2-(Methacryloxy)ethoxycarbonyl]benzenesulfonyloxyimino)benzyl cyanide

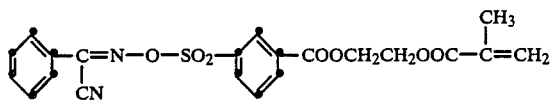

(1a) 3-Chlorosulfonylbenzoyl chloride

This compound is obtained in accordance with the method described in U.S. Pat. No. 3,290,370 by chlorosulfonating α-trichlorotoluene.

(1b) 3-[2-(Methacryloxy)ethoxycarbonyl]benzenesulfonyl chloride

With stirring, a solution of 13 g (0.1 mole) of 2-hydroxyethyl methacrylate in 80 ml of tetrahydrofuran is slowly added dropwise at 0° C. to a solution of 23.9 g (0.1 mole) of 3-chlorosulfonylbenzoyl chloride and 7.9 g (0.1 mole) of pyridine in 150 ml of tetrahydrofuran. The reaction mixture is subsequently stirred for 15 hours at room temperature. The precipitated pyridine salt is removed by filtration, and the filtrate is concentrated by evaporation in vacuo. The oily residue is dried under high vacuum, affording 28 g of viscous product.

Analysis: $C_{13}H_{13}ClO_6S$ (332.74) calc., C, 46.92; H, 3.94; S, 9.63; Cl, 10.65%; found, C, 47.40; H, 4.04; S, 9.49; Cl, 10.36%.

(1c) α-Hydroxyiminobenzyl cyanide

This compound is prepared from benzyl cyanide by reaction with methyl nitrite in $CH_3OH/CH_3ONa$ in accordance with the method described in Org. Synthesis 59, 95 (1979). Colourless crystals with a melting point of 119°–121° C.

(1d) α-(3-[2-(Methacryloxy)ethoxycarbonyl]benzenesulfonyloxyimino)benzyl cyanide With cooling to 0° C. and with stirring, a solution of 16.6 g (0.05 mole) of 3-[2-(methacryloxy)ethoxycarbonyl]benzenesulfonyl chloride (1b) in 50 ml of $CH_2Cl_2$ is added dropwise to a solution of 7.3 g (0.05 mole) of α-hydroxyiminobenzyl cyanide (1c) and 5.05 (0.05 mole) of triethylamine in 100 ml of methylene chloride. The reaction mixture is subsequently stirred for 18 hours at room temperature. Water is then added to the reaction mixture, and the organic phase is separated, washed with water and dried over $MgSO_4$. The solution is concentrated by evaporation, and the oily residue is dried under high vacuum, affording 14.5 g of the title compound as a viscous colourless mass.

Analysis: $C_{21}H_{18}N_2O_7S$ (442.41) calc., C, 57.01; H, 4.10; N, 6.33; S, 7.25%; found, C, 56.92; H, 4.18; N, 6.26; S, 7.03%.

$^1$H-NMR (100 MHz, $CDCl_3$): 8.75 (t, J=2, 1 aromat. H), 8.5–8.2 (m, 2 aromat. H), 7.9–7.35 (m, 6 aromat. H), 6.18 (s with FS, 1 vinylic H), 5.60 (t, J=2, 1 vinylic H), 4.75–4.4 (m, 2 —$CH_2O$—) 1.95 (t, J=2, $CH_3$).

IR spectrum: 2235 w (C≡N), 1720s (CO ester), 1630 w (C=C), 1264 m and 1195 s ($SO_2OR$).

EXAMPLE 2
9-(3-[2-(Methacryloxy)ethoxycarbonyl]benzenesulfonyloxyimino)fluorene

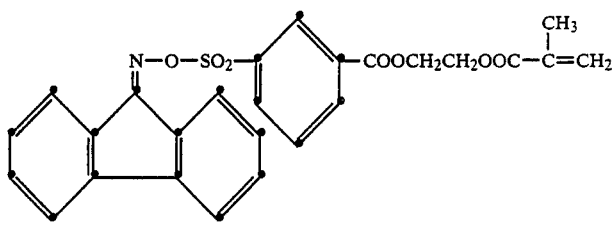

This compound is prepared from fluorenonoxime and 1b in tetrahydrofuran in accordance with a procedure analogous to that of Example 1d. The crude product is a yellow highly viscous mass.

Analysis: $C_{26}H_{21}NO_7S$ (491.7) calc., C, 63.54; H, 4.31; N, 2.85; S, 6.52%; found, C, 63.92; H, 4.31; N, 3.02; S, 6.32%.

IR spectrum: 1720s, 1630w, 1261m, 1190s

The $H^1$-NMR spectrum corresponds with the structure indicated.

EXAMPLE 3
α-(4-Hydroxybenzenesulfonyloxyimino)thien-2-ylacetonitrile

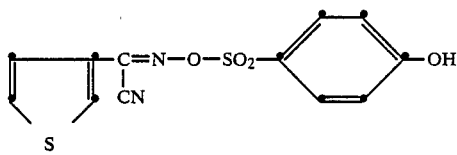

(3a) 4-Acetoxybenzenesulfonyl chloride 270 g of a 65% solution of phenol-4-sulfonic acid in water (1 mole) are stirred together with 100 ml of toluene to give a suspension. With vigorous stirring, first 113 g of KOH (2 moles) in 240 ml of water are added dropwise, followed by the dropwise addition of 110 g (1 mole) of acetic anhydride. The reaction mixture is subsequently stirred for 15 hours at room temperature. 300 ml of water are then added to the reaction mixture, and the aqueous phase is separated and then concentrated by evaporation in vacuo. The residual potassium salt of 4-acetoxybenzenesulfonic acid is washed with hot ethanol and dried.

254 g (1 mole) of the salt so obtained are added in portions to a solution of 416 g (2 moles) of $PCl_5$ in 1 liter of $CCl_4$, which solution has been cooled to 0° C., and the reaction mixture is subsequently stirred for 16 hours at room temperature. The reaction mixture is then poured into ice, and the organic phase is separated, dried over $MgSO_4$ and concentrated by evaporation.

The residual crude product is recrystallized from diethyl ether. Melting point: 76°–78° C.

Analysis: C$_8$H$_7$ClO$_4$S (234.66) calc., C, 40.95; H, 3.01; Cl, 15.11; S, 13.66%; found, C, 40.71; H, 2.94; Cl, 15.15; S, 13.67%.

(3b) α-Hydroxyiminothien-2-ylacetonitrile

This compound is prepared from thiophen-2-acetonitrile and methyl nitrile in accordance with a method analogous to the one described in Org. Synthesis 59, 95 (1979). Yellowish crystals with a melting point of 103°–104° C.

Analysis: C$_6$H$_4$N$_2$OS (152.06) calc., C, 47.36; H, 2.65; N, 18.41; S, 21.07%; found, C, 47.25; H, 2.79; N, 18.21; S, 21.14%.

(3c) α-(4-Acetoxybenzenesulfonyloxyimino)thien-2-ylacetonitrile 200 mg of 4-dimethylaminopyridine and 6.2 g (0.08 mole) of pyridine are added to a solution of 12 g (0.08 mole) of α-hydroxyiminothien-2-ylacetonitrile (3b) in 75 ml of tetrahydrofuran. With cooling to 0° C., a solution of 18.5 g (0.08 mole) of 4-acetoxybenzenesulfonyl chloride (3a) in 30 ml of tetrahydrofuran is added dropwise. The reaction mixture is stirred for 16 hours at room temperature, and 100 ml of diethyl ether are subsequently added. The precipitated salts are removed by filtration and the solution is concentrated by evaporation. The residual crude product is recrystallised from hexane/ethyl acetate, affording 15 g of crystals with a melting point of 114°–115° C.

Analysis: C$_{14}$H$_{10}$N$_2$O$_5$S$_2$ (350.34) calc., C, 47.99; H, 2.88; N, 8.00%; found, C, 47.71; H, 2.94; N, 8.35%.

(3d) α-Hydroxybenzenesulfonyloxyimino)thien-2-ylacetonitrile

With vigorous stirring, a solution of 12 g of NaOH in 20 ml of water is added to a solution of 27 g (0.08 mole) of α-(4-acetoxybenzenesulfonyloxyimino)-thienylacetonitrile (3c) in 125 ml of tetrahydrofuran. After 1 hour, the reaction mixture is acidified with 20% hydrochloric acid and, after the addition of water and diethyl ether, the phases are separated. The aqueous phase is extracted with ether, the combined organic phases are dried over MgSO$_4$, and the solvent is distilled off. The residual crude product is recrystallised from toluene, affording 17 g of beige-coloured crystals which melt at 151°–152° C.

Analysis: C$_{12}$H$_8$N$_2$O$_4$S$_2$ (308.3) calc., C, 46.75; H, 2.62; N, 9.01; S, 20.80%; found, C, 47.19; H, 2.70; N, 8.94; S, 20.27%.

IR spectrum: 3400 and 3300 br(OH), 2225 s (CN), 1375 s (SO$_2$) $^1$H-NMR spectrum (100 MHz, CDCl$_3$): 7.96 (d, 2H) 8.05–7.83 (m, 1H), 7.7–7.55 (m, 1H), 7.25–6.9 (m, 1H), 7.02 (d, 2H), 1.8 (s, OH).

EXAMPLE 4

α-(4-Methacryloxybenzenesulfonyloxyimino)thien-2-ylacetonitrile

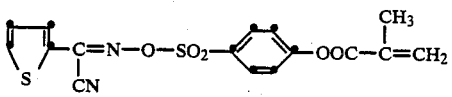

2.2 g (0.022 mole) of triethylamine and 0.5 g of 4-dimethylaminopyridine are added to a solution of 6.1 g (0.022 mole) of α-(4-hydroxybenzenesulfonyloxyimino)thien-2-ylacetonitrile (3a) in 75 ml of methylene chloride. With cooling to 0° C., a solution of 2.3 g (0.022 mole) of methacryloyl chloride in 20 ml of CH$_2$Cl$_2$ is added dropwise, and the reaction mixture is stirred for 3 hours at 0° C. The mixture is then filtered through silica gel, the filtrate is concentrated by evaporation, and the residue is recrystallised from methylene chloride/hexane, affording 5.92 g of the title compound with a melting point of 165°–166° C.

Analysis: C$_{16}$H$_{12}$N$_2$O$_5$S$_2$ (376.38) calc., C, 51.06; H, 3.22; N, 7.44; S, 17.04%; found, C, 50.76; H, 3.05; N, 7.26; S, 17.07%.

The H$^1$-NMR spectrum and IR spectrum correspond with the structure indicated.

EXAMPLE 5

α-(4-Hydroxybenzenesulfonyloxyimino)benzyl cyanide

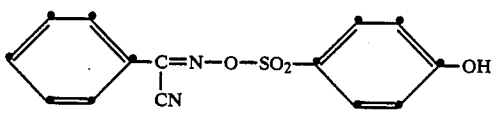

14.6 g (0.1 mole) of α-hydroxyiminobenzyl cynide (1c) are reacted with 23.46 g (0.1 mole) of 4-acetoxybenzenesulfonyl chloride (3a) in accordance with a procedure analogous to that of Example 3c. The resultant α-(4-acetoxybenzenesulfonyloxyimino)benzyl cyanide melts at 142°–143° C. 6 g of this compound are hydrolysed with a solution of NaOH in accordance with a procedure analogous to that of Example 3d, affording the title compound which, after recrystalisation from toluene, melts at 148° C.

Analysis: C$_{14}$H$_{10}$N$_2$O$_4$S (302.3) calc., C, 55.63; H, 3.34; N, 9.27; S, 10.61%; found, C, 55.53; H, 3.55; N, 8.89; S, 10.39%.

IR spectrum: 3415s (OH), 2235 W (CN), 1368s and 1182s (SO$_2$)

The $^1$H-NMR spectrum corresponds with the structure indicated.

EXAMPLE 6

1-(4-Hydroxybenzenesulfonyloxyimino)-1,2,3,4-tetrahydronaphthalene

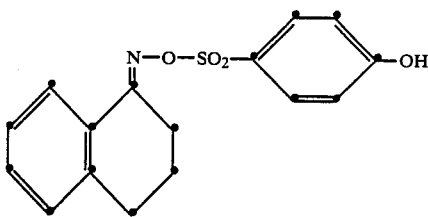

(6a) α-Tetralonoxime

This compound is prepared from α-tetralone and NH$_2$OH.HCl, in the presence of K$_2$CO$_3$ in methanol, in accordance with the method described in Chem. Ber. 54, 57 (1921). Melting point: 101°–104° C.

(6b) 1-(4-Acetoxybenzenesulfonyloxyimino)-1,2,3,4-tetrahydronaphthalene

This compound is prepared from α-tetralonoxime (6a) and 4-acetoxybenzenesulfonyl chloride (3a) in accordance with a procedure analogous to that of Example 3c. Melting point: 151°–152° C.

Analysis: C$_{18}$H$_{17}$NO$_5$S (359.38) calc., C, 60.16; H, 4.77; N, 3.90; S, 8.92%; found, C, 59.94; H, 4.99; N, 3.99; S, 8.92%.

(6c) 1-(4-Hydroxybenzenesulfonyloxyimino)-1,2,3,4-tetrahydronaphthalene

This compound is prepared by alkaline hydrolysis of the above compound (6b) in accordance with a procedure analogous to that of Example 3d. Colourless crystals with a melting point of 141°–142° C.

Analysis: $C_{16}H_{15}NO_4S$ (317.34) calc., C, 60.55; H, 4.76; N, 4.41; S, 10.10%; found, C, 60.49; H, 4.88; N, 4.37; S, 10.17%.

IR spectrum: 3375s, 1348s, 1174s

The $^1$H-NMR spectrum corresponds with the structure indicated.

EXAMPLE 7

1-(4-Methacryloxybenzenesulfonyloxyimino)-1,2,3,4-tetrahydronaphthalene

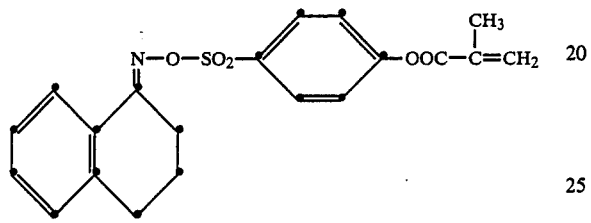

The product of Example 6c is reacted with methacryloyl chloride in accordance with a procedure analogous to that of Example 4. Colourless crystals with a melting point of 108°–109° C.

Analysis: $C_{20}H_{19}NO_5S$ (385.41) calc., C, 62.32; H, 4.97; N, 3.63; S, 8.32%; found, C, 62.11; H, 5.05; N, 3.53; S, 8.30%.

IR spectrum: 1724s, 1622w, 1373s, 1182s

The $^1$H-NMR spectrum corresponds with the structure indicated.

EXAMPLE 8

α-Trifluoroacetophenononoxime 4-hydroxybenzenesulfonate

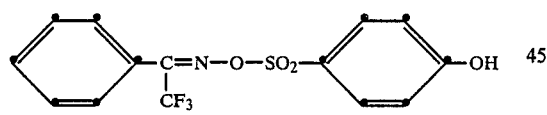

(8a) α-Trifluoroacetophenononoxime

This compound is prepared from trifluoroacetophenone and hydroxylamine in accordance with a procedure analogous to that of Example 6a.

(8b) α-Trifluoroacetophenononoxime 4-acetoxybenzenesulfonate

This compound is prepared by reacting compound 8a with 4-acetoxybenzenesulfonyl chloride (3a) in accordance with a procedure analogous to that of Example 3c. The oily crude product is used for the next reaction step without further purification.

(8c) α-Trifluoroacetophenononoxime 4-hydroxybenzenesulfonate

The acetoxy compound 8b is hydrolysed with NaOH in accordance with a procedure analogous to that of Example 3d. Colourless crystals with a melting point of 120°–121° C.

Analysis: $C_{14}H_{10}F_3NO_4S$ (345.25) calc., C, 48.70; H, 2.92; N, 4.06; S, 9.28; F, 16.50%; found, C, 48.63; H, 2.87; N, 3.97; S, 9.47; F, 16.64%.

IR spectrum: 3385s (OH), 1178s (SO$_2$), 1160, 1155 and 1143s (C-F), 548s (C-F)

$^1$H-NMR spectrum (100 MHz, CDCl$_3$): 7.90 (d, I=8.75, 2 aromat. H), 7.60–7.30 (m, 5 aromat. H), 7.01 (d, I=8.75, 2 aromat. H), 5.98 (s, OH).

EXAMPLE 9

9-(4-Hydroxybenzenesulfonyloxyimino)fluorene

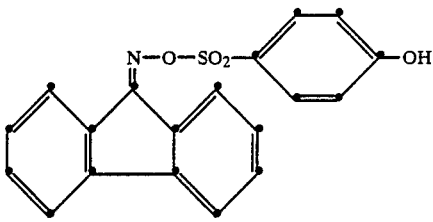

In accordance with a procedure analogous to that of Example 3c, fluorenononoxime is reacted with 4-acetoxybenzenesulfonyl chloride (3a) to give 9-(4-acetoxybenzenesulfonyloxyimino)fluorene which melts at 167°–168° C.

This compound is hydrolysed with NaOH in accordance with a procedure analogous to that of Example 3d, affording the title compound in the form of yellow crystals with a melting point of 216°–217° C.

Analysis: $C_{19}H_{13}NO_4S$ (351.4) calc., C, 64.95; H, 3.73; N, 3.99; S, 9.12%; found, C, 65.10; H, 3.97; N, 3.93; S, 8.60%.

IR spectrum: 3415s, 1370s, 1180s

The $^1$H-NMR spectrum corresponds with the structure indicated.

EXAMPLE 10

9-(4-Bromomethylbenzenesulfonyloxyimino)fluorene

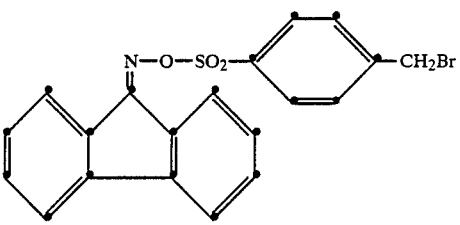

Fluorenonoxime (prepared in accordance with the method of F. J. Moore and E. H. Hunters/J. Amer. Chem. Soc. 49 (1927), (2618) is reacted at 0° C. with one equivalent of p-toluenesulfonyl chloride, in tetrahydrofuran and in the presence of one equivalent of triethylamine. Working up as in Example 3c affords fluorenonoxime tosylate which melts at 155°–160° C.

Analysis: calc., 9.18%, S; found, 9.15%, S.

73.3 g (0.41 mole) of N-bromosuccinimide and 3 g of azobisisobutyronitrile are added to a solution of 144 g (0.41 mole) of the tosylate in 1500 ml of CCl$_4$. The suspension is heated to reflux for 4 hours. After the suspension has cooled, the succinimide is removed by filtration and the filtrate is concentrated by evaporation. The residual crude monobromide is contaminated with dibromide and starting material. Repeated recrystallisation from hexane/tetrahydrofuran yields the pure monobromide which melts at 151°–152° C.

Analysis: $C_{20}H_{14}BrNO_3S$ (428.3) calc., C, 56.09; H, 3.29; N, 3.27; S, 7.49; Br, 18.66%; found, C, 55.86; H, 3.32; N, 3.32; S, 7.51; Br, 18.98%.

IR spectrum: 1368s, 1185s $^1$H-NMR spectrum (100 MHz, CDCl$_3$): 8.35–8.0 m, 7.75–7.1 m, 4.5 s.

EXAMPLE 11

α-(4-Bromomethylbenzenesulfonyloxyimino)benzyl cyanide

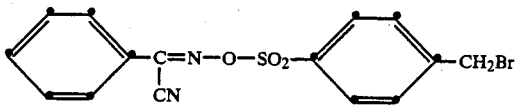

α-Tosyloxyiminobenzyl cyanide is prepared from α-hydroxyiminobenzyl cyanide and p-toluenesulfonyl chloride in accordance with a procedure analogous to that of Example 1d. Melting point: 179°–181° C.

Analysis: calc., 10.67%, S; found, 10.67%, S.

The compound is brominated with bromosuccinimide in tetrachloromethane in accordance with a procedure analogous to that of Example 10. The monobromide obtained after recrystallisation from hexane/tetrahydrofuran melts at 171°–172° C.

Analysis: $C_{15}H_{11}BrN_2O_3S$ (379.20) calc. C, 47.51; H, 2.92; N, 7.39; S, 8.45; Br, 21.07%; found C, 47.62; H, 2.98; N, 7.45; S, 8.70; Br, 20.88%.

IR spectrum: 2225w, 1378s, 1188s $^1$H-NMR spectrum: 8.05d, 7.9–7.35m, 7.64d, 4.51s.

EXAMPLE 12

9-(4-Aminomethylbenzenesulfonyloxyimino)fluorene

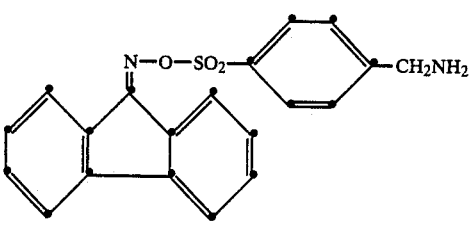

A solution of 28 g (0.2 mole) of hexamethylenetetramine in 350 ml of CHCl$_3$ is added to a solution of 85.7 g (0.2 mole) of 9-(4-bromomethylbenzenesulfonyloxyimino)fluorene (Example 10) in 500 ml of chloroform, and the reaction mixture is stirred for 1 hour at room temperature. The precipitated salt is isolated by filtration and washed with CHCl$_3$. Melting point: 196°–197° C.

Analysis: calc., 14.0%, Br; found, 13.7%, Br.

56.8 g (0.1 mole) of the salt are suspended in a mixture of 88 ml of water and 88 ml of ethanol, and then 42 ml of concentrated hydrochloric acid are added. The reaction mixture is stirred for 12 hours at room temperature and then for 1 hour at 50° C. After the mixture has cooled, NaOH solution is added until a pH value of 8 is attained. The mixture is extracted with methylene chloride, the organic phase is dried and concentrated by evaporation, and the residue is recrystallised from ethanol. Yellowish crystals with a melting point of 106°–107° C.

Analysis: $C_{20}H_{16}N_2O_3S$ (364.4) calc., C, 65.92; H, 4.43; N, 7.69; S, 8.80%; found, C, 66.22; H, 4.66; N, 7.14; S, 8.71%.

IR spectrum: 3400br, 1370s, 1185s $^1$H-NMR spectrum: 8.29d, 8.05d, 7.70–7.10m, 3.69s, 3.4s, 2.15s.

EXAMPLE 13

9-(4-Methacrylamidomethylbenzenesulfonyloxyimino)-fluorene

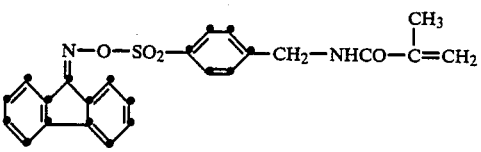

A solution of 2.87 g (0.026 mole) of methacryloyl chloride is added dropwise at 0° C. to a solution of 5 g (0.013 mole) of the product of Example 12 and 2.77 g (0.026 mole) of triethylamine in 50 ml of tetrahydrofuran. The reaction mixture is stirred for 12 hours, and then water and diethyl ether are added. The organic phase is washed with dilute hydrochloric acid, dried over MgSO$_4$ and concentrated by evaporation. The oily crude product is crystallised from hexane/ethyl acetate. Yellowish crystals with a melting point of 187°–188° C.

Analysis: $C_{24}H_{20}N_2SO_4$ (432.46) calc., C, 66.65; H, 4.66; S, 7.41%; Found, C, 66.49; H, 5.13; S, 6.90%.

The IR spectrum and $^1$H-NMR spectrum correspond with the structure indicated.

EXAMPLE 14

α-(4-Carboxybenzenesulfonyloxyimino)benzyl cyanide

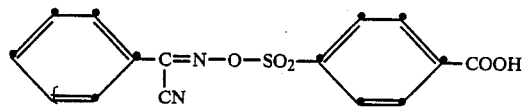

In the temperature range from −10° C. to 0° C. and with stirring, a solution of 7.55 g of p-chlorosulfonylbenzoic acid in 25 g of tetrahydrofuran is slowly added to a solution of 5 g of α-hydroxyiminobenzyl cyanide in 24 g of tetrahydrofuran. The reaction mixture is heated, with stirring, to room temperature. After 2 hours, the reaction mixture is poured into 600 ml of 0.12N hydrochloric acid. The precipitated product is isolated by filtration, washed with water and dried at 40° C. in vacuo. Melting point: 250°–251° C.

The IR spectrum and $^1$H-NMR spectrum correspond with the structure indicated.

EXAMPLE 15

α-(4-Chlorocarbonylbenzenesulfonyloxyimino)benzyl cyanide

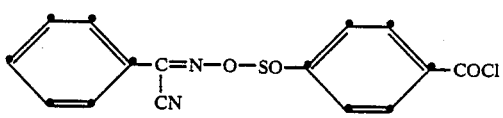

4 g of the product of Example 14 are suspended in 20 g of thionyl chloride, and 0.5 ml of dimethylformamide are added. The reaction mixture is then heated to 50° C.

until the evolution of gas ceases (2 hours) and a clear solution has formed. Part of the excess thionyl chloride is evaporated off, affording a crystaline product which is isolated by filtration and recrystallised from dichloromethane. Melting point: 193°–195° C.

EXAMPLES 16 TO 21

Preparation of copolymers

Compounds of formula I, wherein Y is an ethylenically unsaturated group, are polymerised, unter nitrogen, with various comonomers in methyl ethyl ketone as solvent. The reaction conditions are indicated in Table 1. The polymers, which are obtained after precipitation with hexane, are white to slightly yellow powders which are soluble in many frequently used organic solvents, e.g. tetrahydrofuran, ethyl glycol acetate, ethyl cellosolve, acetone etc., and can be processed to clear films. Table 1 shows the composition, preparatory conditions and properties of the copolymers.

TABLE 1

| Copolymerisation of ethylenically unsaturated oxime sulfonates | | | | | | |
|---|---|---|---|---|---|---|
| Example | 16 | 17 | 18 | 19 | 20 | 21 |
| Monomers(*) | | | | | | |
| MMA (g) | 40.0 | 7.5 | 40.0 | 16.0 | 16.0 | 7.0 |
| MAA (g) | 5.0 | 7.5 | — | 2.0 | — | 1.0 |
| EHMA (g) | — | 27.5 | — | — | — | — |
| oxime sulfonate (g) of | | | | | | |
| Example 1 | — | — | — | 2.0 | 4.0 | — |
| Example 2 | 10.0 | 15.0 | 20.0 | — | — | — |
| Example 7 | — | — | — | — | — | 2.0 |
| Polymerisation conditions(*) | | | | | | |
| MEK (ml) | 150 | 150 | 150 | 100 | 100 | 50 |
| AIBN (g) | 0.5 | 0.52 | 0.48 | 0.20 | 0.20 | 0.08 |
| temp. (°C.) | 80 | 80 | 80 | 83 | 80 | 83 |
| time (h) | 10 | 10 | 10 | 7.5 | 8.0 | 24 |
| yield (g) | 54.8 | 50.4 | 54.8 | 16.3 | 16.3 | 9.6 |
| characterisation of the copolymers(*) | | | | | | |
| S content (%) | 1.03 | 1.54 | 1.86 | 0.70 | 1.45 | 1.49 |
| $M_w$ (GPC) | 22500 | 37200 | 26400 | 15400 | 13800 | 6700 |

(*)legend
MMA methyl methacrylate
MAA methacrylic acid
EHMA 2-ethylhexyl methacrylate
AIBN α,α'-azobisisobutyronitrile
MEK methyl ethyl ketone
$M_w$ (GPC) average molecular weight (weight average) determined by gel permeation chromatography in tetrahydrofuran

EXAMPLES 22 TO 24

Production of positive images from copolymers

20% solutions in ethyl glycol acetate of the copolymers of Examples 16 to 21 are prepared, and 0.2% by weight (based on the weight of the copolymer) of Orasol Red B and 2% by weight of 9-methylanthracene are added to each solution. Transparent polyester sheets are coated with these solutions by means of a 20 μm doctor knife and the layers are then dried for 3 minutes at 100° C. Hard polymer layers of about 3 μm thickness are obtained. The sheets are then exposed to the radiation of a mercury high pressure lamp through a mask with a linear pattern (line width: 0.5 μm to 5 μm) and subsequently developed in an aqueous alkaline developer for 1 to 2 minutes. Positive images with a resolution of better than 1 μm are obtained.

A solution containing copolymer 16 is processed as described above and the layer is exposed to radiation for 30 seconds. After development for 2 minutes in a mixture comprising 200 ml of positive developer C 1290 (Horsell Graphic Industries, Morley, England), 10 g of sodium hydroxide and 50 ml of 2-ethoxyethanol, with simultaneous gentle rubbing with a cotton swab, a positive image with a resolution of 1 μm is obtained.

A layer of copolymer 18 is prepared as described above and exposed to radiation through the mask for 30 seconds and 60 seconds. Development is carried out for 2 minutes in a basic developer consisting of 100 ml of 1-methoxy-2-propanol, 50 ml of positive developer C 1290 and 5 g of NaOH, with simultaneous rubbing with a cotton swab. Only the sample which has been exposed to radiation for 60 seconds is fully developed. However, this sample produces a very good positive image with a resolution of better than 1 μm.

EXAMPLE 25

Preparation of a modified novolak resin 3 g of novolak resin (prepared from phenol, p-tert-butylphenol and formaldehyde in a molar ratio of 0.75:0.25:0.90; softening temperature: 120° C.) are dissolved in 12 g of pyridine. 1 g of the acid chloride of Example 15 is added. The mixture is stirred for 2 hours and then poured into 600 ml of 0.2N hydrochloric acid. The solid product is isolated by filtration and dried. The product is subsequently dissolved in acetone and again precipitated in 600 ml of 0.02N hydrochloric acid, isolated by filtration, washed with water and dried in vacuo at 40° C.

EXAMPLE 26

Production of a positive image from modified novolak 1 g of the modified novolak of Example 25 is dissolved in 2.3 ml of a solvent mixture comprising 2-ethoxyethanol, 2-ethoxyethyl acetate and ethyl methyl ketone (volume ratio 2:2:1), and 2 drops of a solution of crystal violet in the same solvent mixture are then added. The resultant solution is subsequently applied as a film to a cleansed, copper-coated laminate plate. After drying has been effected for 5 minutes at 90° C., a varnish layer of 5 μm thickness is obtained. The layer is exposed through a negative to the radiation of a 5000 W metal halide lamp at a distance of 75 cm for 1 minute. Development is carried out in a 10% aqueous solution of sodium carbonate, whereby the exposed areas are washed out. A good positive image is produced.

What is claimed is:

1. A compound of formula I

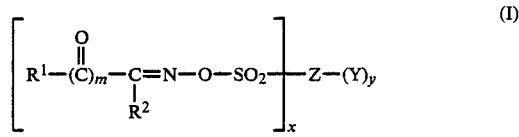

wherein
m is 0 or 1,
x is 1 or 2,
y is 1 or 2,
$R^1$ is $C_1$–$C_{12}$-alkyl, $C_1$–$C_4$-haloalkyl, $C_5$–$C_{12}$-cycloalkyl, $C_6$–$C_{10}$-aryl or said aryl substituted by one or more of the substituents selected from the group consisting of halogen, $C_1$–$C_6$-alkyl, $C_1$–$C_4$-alkoxy, phenoxy, phenyl and nitro, or $R^1$ is furyl, thienyl, $C_7$–$C_{12}$-aralkyl, $C_1$–$C_8$-alkoxy, $C_5$–$C_8$-cycloalkoxy, phenoxy or —CN, R² has one of the meanings indicated for R¹, or R² is C₂–C₆-alkanoyl, benzoyl, C₂–C₅-alkoxycarbonyl, phenoxycarbonyl, —N(R³)(R⁴), morpholino or piperidino, or R¹ and R², together with the atoms to which they are attached, form a 5- or 8-membered ring which may be fused with 1 or 2 radicals of the benzene series, R³ is hydrogen, C₁–C₁₂-alkyl, phenyl, C₂–C₆-alkanoyl or benzoyl, R⁴ is hydrogen, C₁–C₁₂-alkyl or cyclohexyl, Y is a polymerizable ethylenically unsaturated group selected from the group consisting of vinyloxy, vinyloxycarbonyl, isopropenyloxy, isopropenyloxycarbonyl, allyloxy, allyloxycarbonyl, methallyloxy, methallyloxycarbonyl, acryloxy, methacryloxy, acrylamido, methacrylamido, allylamino, diallylamino, maleinimido and itaconimido; or Y is an epoxide group of the formula

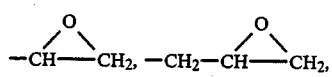

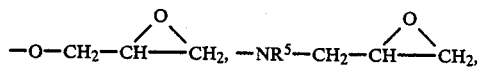

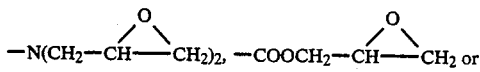

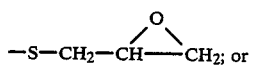

Y is an —OH, —NHR⁵, —COOH, —COOR⁶, —COCl, —SO₂Cl or —NCO groups,

R⁵ is hydrogen, C₁–C₆-alkyl or phenyl,

R⁶ is C₁–C₆-alkyl or phenyl, and

Z is a 2-, 3- or 4-valent aromatic or aromatic-aliphatic group of the formula

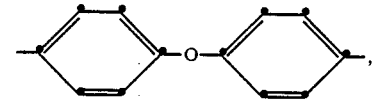

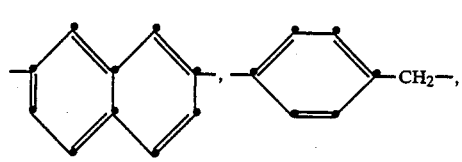

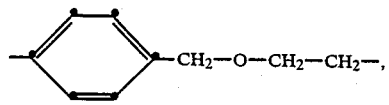

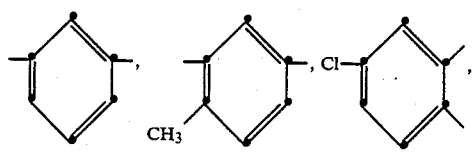

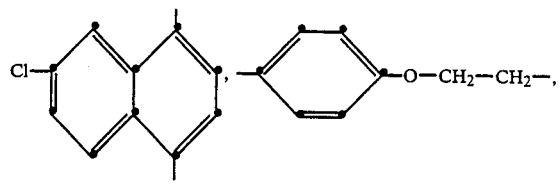

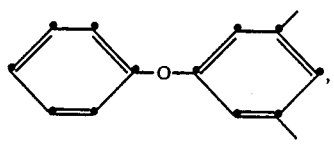

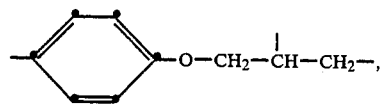

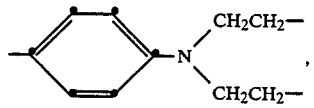

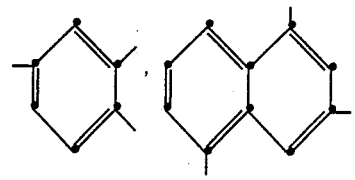

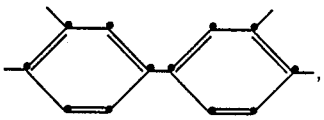

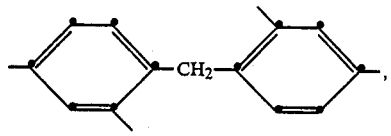

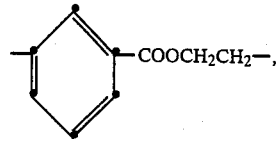

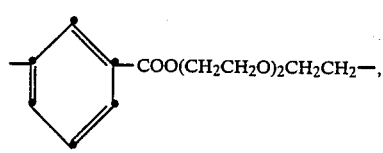

-continued

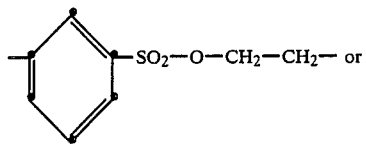

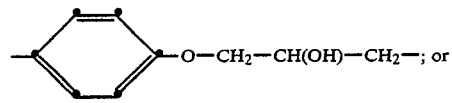

Z is straight or branched chain $C_1$-$C_{12}$-alkylene, —CH$_2$CH$_2$OCH$_2$CH$_2$—, —(CH$_2$CH$_2$O)$_2$CH$_2$CH$_2$—, —CH$_2$CH$_2$SCH$_2$CH$_2$— or —CH$_2$CH$_2$NHCH$_2$CH$_2$—, or Z is an aliphatic or cycloaliphatic group of the formula

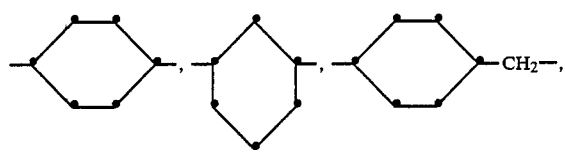

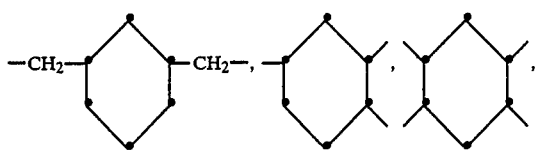

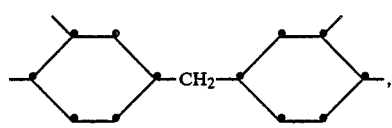

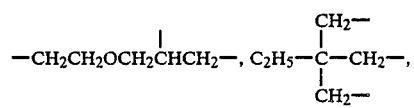

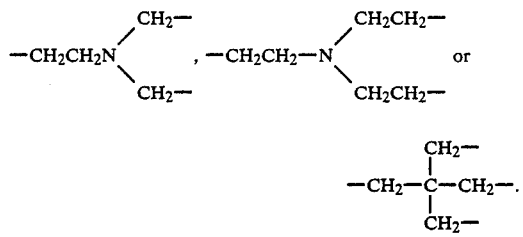

2. A compound according to claim 1 of formula I, whereby y is 1 and Y is a group of the formula

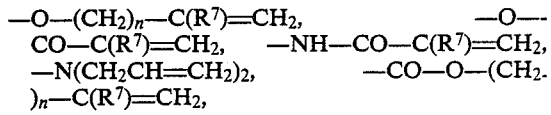

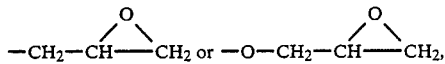

in which formulae n is 0 or 1 and $R^7$ is hydrogen or methyl.

3. A compound according to claim 1 of formula I, wherein y is 2 and Y is an epoxide group or an —OH, —NHR$^5$, —COOH, —COOR$^6$, —COCl, —SO$_2$Cl or —NCO group.

4. A compound according to claim 1 of formula I, wherein y is 1 and Y is an epoxide group or an —OH, —NHR$^5$, —COOH, —COOR$^6$, —COCl, —SO$_2$Cl or —NCO group.

5. A compound according to claim 1 of formula I, wherein x is 1, $R^1$ is $C_1$-$C_6$alkyl, $C_1$-$C_4$haloalkyl, phenyl or phenyl substituted by 1 or 2 substituents selected from the group consisting of chlorine, $C_1$-$C_4$alkyl, $C_1$-$C_4$alkoxy and nitro, or is 2-furyl, 2-thienyl, $C_1$-$C_4$alkoxy or —CN, $R^2$ has one of the meanings indicated for $R^1$ or is dialkylamino or morpholino, or $R^1$ and $R^2$, together with the atoms to which they are attached, form a 5- or 6-membered ring which may be fused with 1 or 2 radicals of the benzene series.

6. A compound according to claim 5 of formula I, wherein m is 0 or 1, $R^1$ is $C_1$-$C_4$alkyl, trifluoromethyl, phenyl, monochlorophenyl, dichlorophenyl or methoxyphenyl, $R^2$ has one of the meanings indicated for $R^1$ or is —CN, or $R^1$ and $R^2$, together with the carbon atom to which they are attached, form an indene, fluorene, tetraline or dihydroanthracene ring.

7. A compound according to claim 1 of formula I, wherein Z is phenylene, naphthylene, $C_2$-$C_6$alkylene, benzylene or a

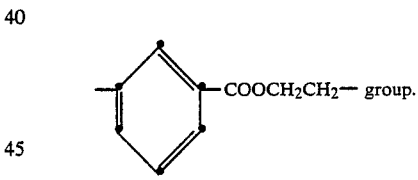

8. The compound according to claim 1 which is 9-(3-[2-(methacryloxy)ethoxycarbonyl]benzenesulfonyloxyimino)fluorene.

9. The compound according to claim 1 which is alpha-(3-[2-(methacryloxy)ethoxycarbonyl]benzenesulfonyloxyimino)benzyl cyanide.

10. The compound according to claim 1 which is 1-(4-methacryloxybenzenesulfonyloxyimino)-1,2,3,4-tetrahydronaphthalene.

* * * * *